United States Patent [19]

Stockdale et al.

[11] Patent Number: 4,501,164

[45] Date of Patent: Feb. 26, 1985

[54] AUTOMATIC SAMPLING ARRANGEMENT

[75] Inventors: Trevor J. Stockdale, Cambridge; John E. Churchill, Haslingfeld, both of England

[73] Assignee: U.S. Philips Corporation, New York, N.Y.

[21] Appl. No.: 520,877

[22] Filed: Aug. 5, 1983

[30] Foreign Application Priority Data

Aug. 20, 1982 [GB] United Kingdom ................ 8223963

[51] Int. Cl.$^3$ ...................... G01N 35/04; G01N 35/06
[52] U.S. Cl. ................................... 73/864.25; 422/64; 73/864.21
[58] Field of Search ........... 73/864.81, 864.21, 864.22, 73/864.23, 864.24, 864.25; 422/64; 141/130

[56] References Cited

U.S. PATENT DOCUMENTS

| | | | |
|---|---|---|---|
| 3,240,070 | 3/1966 | Martin et al. | 73/864.23 |
| 3,301,005 | 1/1967 | Fahrenbach et al. | 73/864.24 |
| 4,118,280 | 10/1978 | Charles et al. | 422/64 X |
| 4,271,123 | 6/1981 | Curry et al. | 422/64 |
| 4,429,584 | 2/1984 | Beyer et al. | 73/864.21 |

Primary Examiner—Jerry W. Myracle
Assistant Examiner—Tom Noland
Attorney, Agent, or Firm—Paul R. Miller

[57] ABSTRACT

In automatic sampling arrangements for supplying liquid samples to analytical instruments, it is convenient to have the samples in open bottles (21) in circular ranks (16), (17) in a turntable (1) indexed in rotation under a sampling mechanism (27). It is desirable to maintain the turntable horizontal while being inserted into a compartment (4) containing the sampling mechanism and a turntable drive assembly (24). Also, for easy operation, it is desirable that the turntable need not be registered accurately in the compartment. The arrangement is constructed so that the turntable is inserted, via an aperture (6) into the compartment in a direction perpendicular to its axis of rotation. The turntable is located by three bearing surfaces (29), (31) and (24) which engage the circumference of the turntable, the driving assembly (24) being one of the bearing surfaces and also engaging the circumference to rotate the turntable. One of the bearing surfaces (31) is movable from a first position in which it engages the circumference to a second position clear of the aperture to allow insertion or withdrawal of the turntable.

11 Claims, 10 Drawing Figures

AUTOMATIC SAMPLING ARRANGEMENT

CROSS-REFERENCE TO RELATED APPLICATION

This application is related to applicants copending application Ser. No. 520,878 also filed on Aug. 5, 1983 which claims a different feature of the sampling arrangement disclosed herein.

BACKGROUND OF THE INVENTION

This invention relates to an automatic sampling arrangement for supplying liquid samples to an analytical instrument such as an atomic absorption spectrophotometer. An atomic absorption spectrophotometer having automatic microprocessor controlled means for carrying out a succession of analyses is described in U.K Patent Application Nos. 8133968 (PHB 32832); 8201371 (PHB 32848); 8201372 (PHB 32849) and 8201373 (PHB 32850) and is manufactured and sold by Pye Unicam Limited under the type number PU9000. It is desirable for the samples to be made available to such an instrument under the control of the microprocessor.

An automatic sampling arrangement is known from published European Patent Application No. 0,015,025 (PP 1234) for supplying liquid samples to an analytical instrument, in this case a flameless atomic absorption spectrophotometer. This sampling arrangement comprises a compartment within which a sample carrier in the form of a turntable may be located, the turntable having a plurality of locations for sample containers arranged on a circle centered on the axis of rotation of the turntable, and a sampling mechanism for aspirating a sample from a sample container when the turntable is indexed to bring one of the sample locations in registration therewith. In this known sampling arrangement the turntable has only one circular rank of sample locations and also the details of the analytical function to be performed on each sample are encoded on the turntable by mechanical means comprising corresponding circular ranks of holes which are either left open or blocked to form a code corresponding to the function. The turntable is mounted on a central spindle.

SUMMARY OF THE INVENTION

It is an object of the invention to provide an automatic sampling arrangement including a turntable in which the turntable can be loaded into a compartment rapidly and without need for careful alignment of the turntable with any part of the compartment.

The invention provides an automatic sampling arrangement for supplying liquid samples to an analytical instrument comprising a compartment within which a sample carrier in the form of a turntable may be located, the turntable having a plurality of locations for sample containers arranged on a circle co-axial with on the axis of rotation of the turntable, and a sampling mechanism for aspirating a sample from a sample container when the turntable is indexed to bring one of the sample locations in registration therewith, characterised in that the arrangement is constructed so that the turntable is inserted, in operation, into the compartment in a direction perpendicular to its axis of rotation, that the turntable is located by three bearing surfaces which engage the circumference of the turntable, that a driving assembly is provided which engages said circumference to rotate the turntable, and that one of the bearing surfaces is movable from a first position in which it engages said circumference to a second position to allow insertion on withdrawal of the turntable. The mechanical arrangements within the compartment are simplified if one of the three bearing surfaces comprises said driving assembly and also if one of said bearing surfaces is mounted so as to resiliently urge the turntable into engagement with the other two bearing surfaces. In a preferred embodiment the driving assembly is also the bearing surface used to apply force resiliently to the turntable. To achieve low driving power, the bearing surfaces are preferably rollers mounted for rotation about axes parallel to the turntable axis, the rollers engaging a cylindrical portion of the turntable circumference.

Insertion of the turntable into the compartment is considerably eased if it is not necessary to place the turntable onto a central drive spindle or to register the turntable on a rotating powered platform. To this end, cut-outs are provided at intervals around the turntable circumference and the drive assembly comprises means for engaging the cut-outs to impart tangential motion to the circumference. The portion of the circumference provided with cut-outs is then axially separated from that portion of the circumference on which the rollers bear.

The position of a desired sample container around the circular rank of locations can be reduced to a counting operation if the cut-outs are spaced at intervals around the circumference corresponding to the spacing of locations around the turntable and if a cut-out detector is provided in the compartment to generate a control signal for the driving assembly when a desired sample location is in registration with the sampling mechanism. Since the cut-out detector then cooperates with the turntable circumference, it will come into registration with the circumference as the turntable is driven into its centered location by the movable bearing surface, reducing the precision which which the turntable needs to be inserted into the compartment. The cut-out detector signals are counted from a predetermined and distinctive initial cut-out corresponding to an initial location. The counting operation takes place within the microprocessor and hence provides the turntable angular location for use in driving the turntable to a desired location under automatic control.

To ease turntable insertion still further the arrangement may be characterised in that the compartment comprises an aperture, closable by a door, through which the turntable is inserted, and in that the door is coupled to the movable bearing surface so that with the door open the movable bearing surface is in its second position and with the door closed the movable bearing surface is in its first position. The turntable may then be inserted by hand as far into the compartment as it will go and the door shut. Automatically, the turntable will then be driven to its centered location with the cut-out detector and the drive assembly engaging the cut-outs. When driven in rotation the weight of the turntable may be carried by the compartment floor. In this event, to reduce the power requirement of the driving assembly, low friction pads may be arranged between the turntable base and the floor, preferably attached to the floor evenly spaced around a circle centered on the turntable axis.

An embodiment of the invention will now be described, by way of example, with reference to the accompanying drawings, in which:

DESCRIPTION OF THE PREFERRED EMBODIMENT

Figure 1:
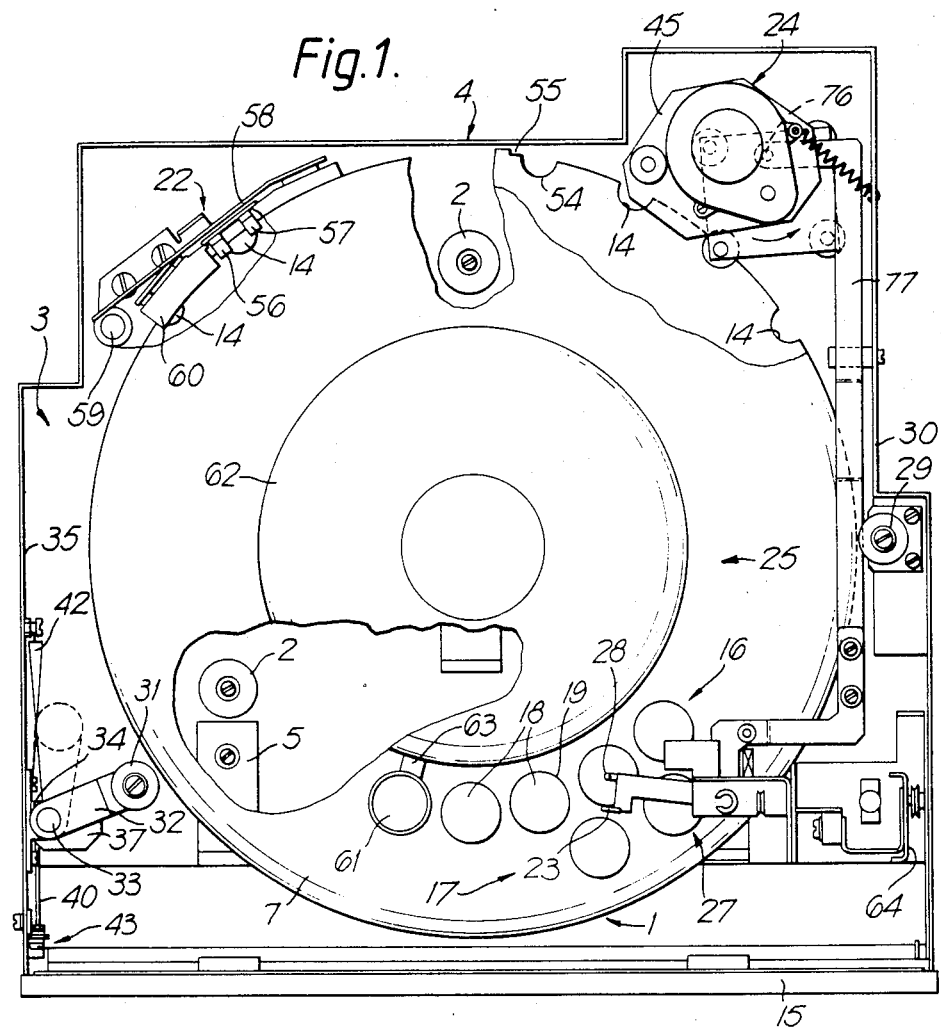
FIG. 1 shows a plan view of a turntable compartment with an upper cover removed to show a turntable in place, registering with a drive assembly at the rear of the compartment, and adjacent to a sampling mechanism at the front of the compartment.
Figure 2:
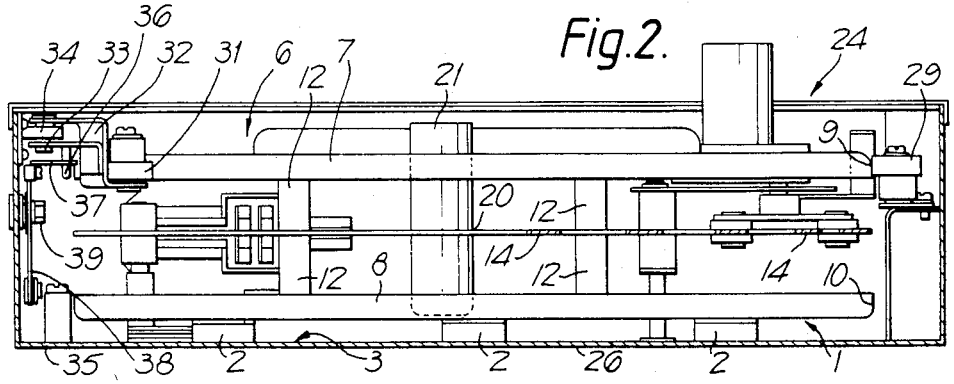
FIG. 2 shows a front view of the turntable compartment with the door and sampling mechanism removed but the turntable in place.

Referring to FIGS. 1 and 2 a flat based cylindrical turntable 1 is shown resting on low-friction pads 2 on a floor 3 of a turntable compartment 4. Chamfered skids 5 are provided to ease sliding insertion of the turntable through aperture 6, shown with a door 15 removed in FIG. 2. The turntable comprises equal diameter upper and lower circular plates 7, 8 with turned-up rims 9 and 10, between which is bolted a flat center plate 11, spaced apart from the upper and lower plates 7, 8 by spacers 12. Plate 11 which is coaxial with plates 7 and 8, has a circular rim 13 having regularly spaced semi-circular cut-outs 14 of which only a few are shown for clarity.

The turntable 1 has two circular ranks, 16 and 17, of regularly spaced locations 18, of which only a few are shown for clarity. Each location comprises aligned holes 19 and 20 in the upper plate 7 and the centre plate 11 to receive an open-necked sample container, or bottle, 21 which may contain a liquid to be sampled and which rests on the lower plate 8. The neck of each bottle stands proud of the upper surface of plate 7 by an amount sufficient to contact a sensor arm 23, to be described later, which can detect the presence of a bottle and initiate a sampling process by the sampling mechanism 27. The cut-outs 14 are equal in number to the number of locations in one of ranks 16 or 17. A cut-out detector 22, to be described in detail later, can detect when a cut-out is aligned with the detector and also when two adjacent cut-outs are spaced either side of the detector and provides two corresponding signals. The locations in the outer rank 17 are spaced between the locations of the inner rank 16 and hence a cut-out detector signal is available when each location in both ranks is at a predetermined angular location in the compartment. A turntable rotation drive assembly 24, to be described in detail later, engages cut-outs 14 to impart tangential motion to rim 13, rotating the tray 1 in the direction of the arrow 25.

The door 15 is hinged about the lower bottom edge 26 and, when fully opened, provides a horizontal sliding surface having low friction skids which is coplanar with the compartment floor 3 and which eases sliding insertion of the turntable into the compartment through aperture 6. The turntable can be so inserted without care being taken to avoid obstacles or to offer the turntable in any particular angular alignment relative to the drive assembly 24 or the sampling mechanism 27 or to position the center of the tray on a spindle. When the door is closed the turntable axis is automatically driven into a predetermined position relative to the sampling mechanism by a mechanism, to be described, linked to the door motion and which mechanism is retracted clear of the aperture 6 with the door open. In addition the door motion is also linked by a further mechanism, to be described, to means for lifting a sample tube 28 and the bottle sensor 23 clear of the aperture 6 when the door is open so that the tray can be inserted freely.

The principle employed to register the turntable, or sample tray, in a predetermined position relative to the compartment floor, and hence to the sampling mechanism, in a manner in which the tray is freely rotatable about its axis is to register a smooth circular rim of the tray against two rollers set in predetermined locations on the floor. The rollers are journalled to rotate freely about vertical axes and hence to roll around the rim, preferably the turned down rim 9 of the upper circular plate 7. A third roller in contact with a point on a rim is mounted to resiliently urge the tray into contact with the two fixed rollers, thereby maintaining the tray axis at a predetermined location on the floor. Ideally, the three rollers would be spaced at intervals of 120 degrees around the tray, enclosing the tray axis and ensuring a stable tray position in spite of disturbing displacements, shocks, etc. However this ideal roller spacing would require that at least one roller would need to be returnably displaced from its predetermined location through a large distance to the side of the compartment for tray insertion. Advantage is taken of the fact that adequate stability of tray position can be ensured with increased intervals of some of the rollers and decreased intervals for others provided that the triangle formed by the roller centers encloses the tray axis with a reasonable margin between the triangle sides and the tray axis.

Figure 3:
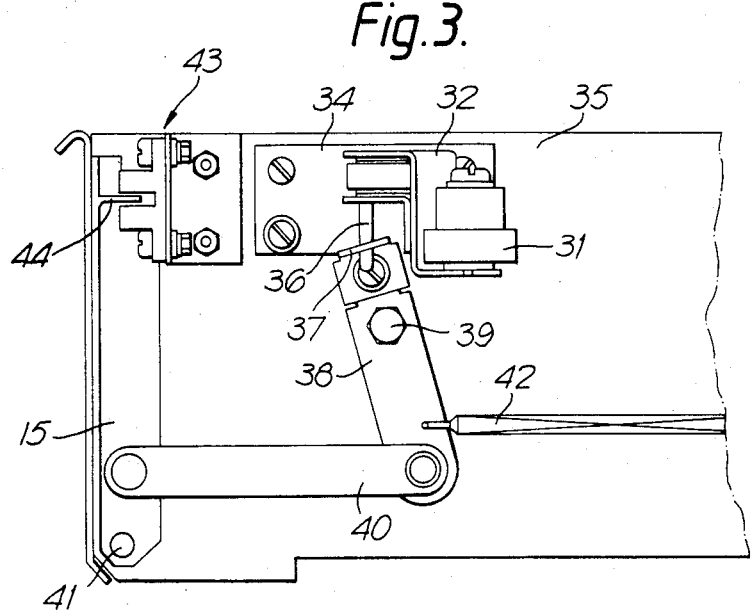
FIG. 3 shows a side view of a door-operated mechanism for locating the turntable in the compartment.

One of the rollers 29 is positioned in the center of one side 30 of the compartment. Thus roller 29 offers no obstruction to tray entry and provides a roller easing tray entry. The second roller 31 is journalled about a vertical axis on a lever arm 32 pivoted about a vertical axis 33 in a rigid casting 34 bolted to the side 35, see also FIG. 3. A vertical peg 36 attached to the underside of lever arm 32 engages with a slot, not shown, parallel to the door face, in the horizontal portion 37 of a cranked lever 38 pivoted about a horizontal axle 39 fixed to side 35. The lever 38 is coupled via a link 40 to door 15 to drive peg 36 into the compartment when the door pivots open about horizontal axis 41. Rearward motion of peg 36 swings lever arm 32 and roller 31 back into the compartment and up against side 35. In this position the roller 31 also provides a roller on the opposite side of the compartment from roller 29 which eases tray entry.

With the tray inserted into the compartment far enough for door 15 to be closed, closure of the door pulls peg 36 towards the front of the compartment, swinging lever arm 32 and roller 31 out into contact with the upper, turned-down rim 9 of the upper plate 7. Initially, roller 31 will drive tray 1 across the compartment into contact with roller 29. Thereafter, since the line joining the centers of rollers 31 and 29 passes to the front of the tray axis, roller 31 will drive the tray further into the compartment. Finally, with door 15 fully closed and held closed by spring 42 in tension between lever 38 and side 35, roller 31 reaches a predetermined location on the floor, defining a predetermined position for the tray relative to the sampling station when in contact with both roller wheels. Tray driving and sampling must not be carried out unless the tray is in the predetermined position. A signal is provided by an opto-electronic detector 43 and fed to driving and sampling control circuits to inhibit operations unless door 15 is closed. Detector 43 comprises a light-emitting diode opposite a photodiode between which a vane 44, attached to the door, cuts off light transmission with the door closed. The photodiode current provides the inhibition signal.

Figure 4:
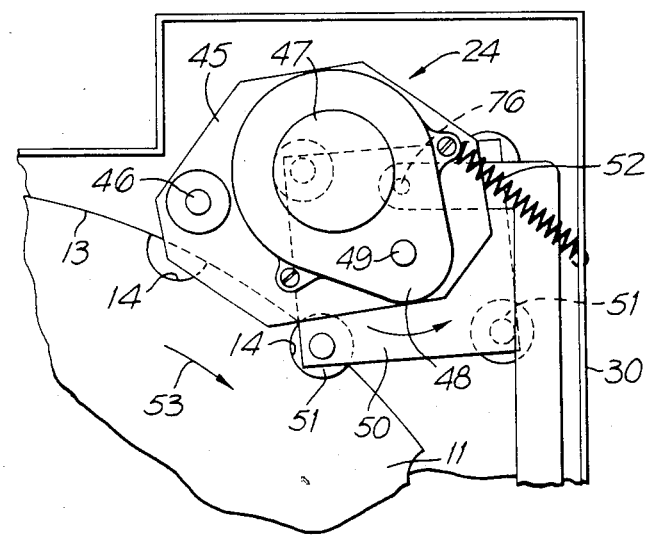
FIG. 4 shows an enlarged plan view of the drive assembly.
Figure 5:
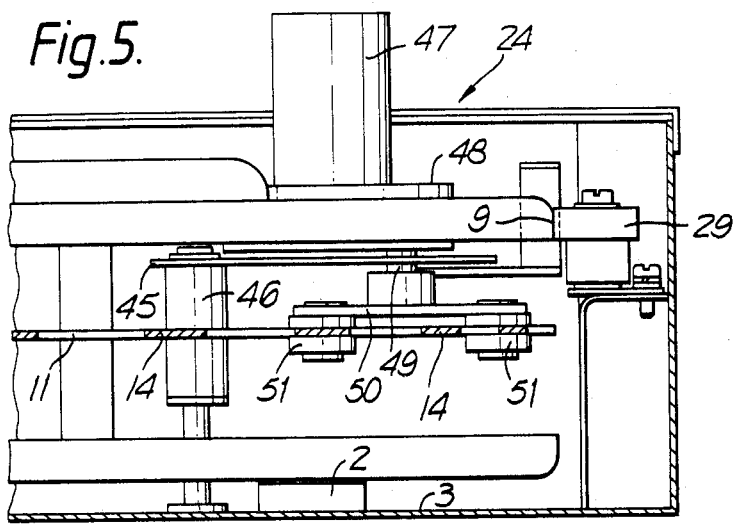
FIG. 5 shows an enlarged front view of the drive assembly.

Referring to FIGS. 1 and 2 and also to the enlarged FIGS. 4 and 5, the drive assembly 24 comprises a motor plate 45 parallel to the floor and pivoted about an axis 46 normal to the floor. An electric drive motor 47 and reduction gear box 48 are mounted on plate 45 and coupled to a drive plate shaft 49 journalled in the motor plate about an axis normal to the motor plate and offset from axis 46 in the tangential direction of rim 13. The drive plate 50 is square and fixed normally at its center to the drive plate shaft 49. The four drive rollers 51, of equal radius, are journalled for free rotation on the corners of the drive plate about axes normal to the plate and are therefore spaced at regular intervals around a circle centered on the drive plate shaft. The cut-outs 14 on plate 11 of the tray are semicircular and of a radius fitting that of the drive rollers 51. Spring 52, in tension between side 30 and motor plate 45, permits resiliently resisted rotation of plate 45 about axis 46. As the tray is inserted in the compartment and driven to its predetermined location by roller 31 as door 15 is closed, some part of rim 13 will come into contact with one or two of rollers 51, driving motor plate 45 and the drive plate 50 rearwards against spring 52. With door 15 finally closed, spring 52, acting via the motor plate, the drive plate and rollers 51, resiliently urges tray 1 forward, ensuring contact between rim 9 and rollers 29 and 31. When tray rotation is required motor 47 is energised by control circuits, rotating drive plate 50 clockwise via gearbox 48. Initially, the roller 51 in contact with rim 13 rolls along the rim without causing tray rotation. Eventually, either the roller in contact or the following roller drops into positive engagement with a cut-out 14 under pressure from spring 52 and thereafter imparts tangential motion as shown by arrow 53 to the rim, rotating the tray 1 about its axis in rolling contact with rollers 29 and 31 and in sliding contact with pads 2.

The above drive assembly dispenses with a central drive shaft for the tray over which the tray would be placed requiring additional height in the compartment. Another alternative might have been a powered turntable on which the tray would be registered. Both these alternative require mechanisms probably including an electric drive motor to be placed under the tray where they would be susceptible to corrosion from sample spillage. In the present design there are only slide surfaces under the tray and the tray location and drive assembly are located at the edges of the top of the tray. The drive motor, in particular, is above the tray.

The tray is indexed in rotation to bring a preselected location under the sample tube using a signal from the cut-out detector 22, mentioned before, to de-energise motor 47 when a cut-out corresponding to the desired sample location is detected. The pre-selected sample location is identified by counting around the locations in the ranks from an initial location corresponding to an initial cut-out 54 identified by an extension 55 along the rim 13. The cut-out detector comprises two opto-electronic detectors 56 and 57 of the same type as door condition detector 43, each giving binary signals corresponding to rim or cut-out being present. If the separation between detectors 56 and 57 is chosen to be greater than the width of a normal cut-out 14 but less than the length of rim between adjacent normal cut-outs, light can only be received by one of detectors 56 and 57, at most. Thus, at the onset of light on one detector the other detector will be obscured by rim, giving rise to two distinguishable logic conditions of the detector outputs as the leading edge of a cut-out just clears one detector or the other. The angular separations between these two logic conditions are not equal since the length of a cut-out is less than the length of rim between adjacent cut-outs. Advantage is taken of this fact to allow for the circumstance that, although the locations in the inner rank are positioned mid-way between the locations in the outer rank, the sample tube 28 is moved from one rank to the other along a path which is inclined to the tray radial direction by the sampling mechanism to be described later. Thus the angle of tray rotation required to move from a location in the outer rank to an adjacent location in the inner rank is less than that required to move on to the next adjacent location in the outer rank. The ratio between cut-out length and intervening rim length can be chosen to provide positioning of the sample tube over the center of a location in either rank.

The extension 55 to the initial cut-out 54 is sufficient to uncover both detectors simultaneously for a small range of tray angles between adjacent cut-outs. Thus a third distinctive logic combination of the detector outputs is available indicating that the leading edge of the initial cut-out has just cleared detector 57 and that therefore the initial location is present at the sampling mechanism. This initial location has been chosen as a location 61 for washing the sample tube 28 to remove contamination. A bottle at location 61 is filled with clean water maintained at a constant level from a central reservoir 62 via pipe 63. A control counter is zeroed on receipt of the third logic combination and a subsequent occurrence of either of the first two logic combinations increases the counter content by one. Thus a desired sample can be identified from the counter output. Detectors 56 and 57 are resiliently mounted upon a carriage 58 pivoted about axis 59 normal to the floor and spring-loaded towards the tray. Chamfered cheeks 60, one above and one below rim 13, provide a generous lead-in for rim 13 to engage the opto-electronic detector gaps correctly on tray insertion.

FIGS. 6 to 10 show views of the sampling mechanism 27, shown in plan view in FIG. 1, looking into aperture 6. The mechanism is mounted upon a vertical tower 64 fixed to the floor 3 of the compartment 4 to the side of aperture 6 to leave the latter clear for turntable insertion. A vertical rod 65 attached to the tower provides a vertical slide for a carriage 66 having tubular bearings 67 which permit both rotatory and vertical motion of the carriage. A cord 68 is attached to carriage 66 via a spring 69 and passes freely through a hole in guide plate 70 attached to carriage 66. Cord 68 passes over pulleys 71 and 72, down tower 64, around pulley 73 and is attached to the compartment door 15 above the door hinge axis 41. A ferrule 75 is clamped to cord 68 under guide plate 70. Spring 69 is relatively weak compared to spring 74. With door 15 closed, carriage 66 rests on the lower support bracket for rod 65, ferrule 75 being then clear of the underside of plate 70. Spring 74 is not extended at all in this condition but spring 69 maintains tension in cord 68, preventing it jumping off the pulleys 71, 72 and 73. As door 15 is opened downwards into a horizontal position for turntable insertion, ferrule 75 first comes in contact with plate 70 whereafter carriage 66 is lifted up until the upper bearing 67 contacts the upper support bracket for rod 65. Damage is prevented by the extension of spring 74 after this contact is made. Thus carriage 66 is lifted by a controlled amount when the door is opened to clear aperture 6 of all parts of the sampling mechanism for turntable insertion.

In use the carriage 66, carrying all remaining parts of the sampling mechanism, is rotated about rod 65 to position sample tube 28 over the inner or outer rank of locations on the turntable. To this end, the carriage 66 extends across the turntable at an angle to the turntable radial direction at the sampling mechanism so that sample tube 28 is moved along a path inclined to this radial direction as mentioned before. This movement of carriage 66 is made in synchronism with the movement of locations past the sampling mechanism by making use of a synchronised radial motion of motor plate 45, see FIGS. 1 and 4, which arises during operation of the drive assembly 24 to rotate the turntable. FIG. 4 shows the position of drive plate 50 in which one of rollers 51 is engaged in a cut-out 14 with the drive plate shaft 49 at its greatest distance from rim 13. In this position, motor plate 45 is pivoted about axis 46 anti-clockwise to the greatest extent, carrying a peg 76 on motor plate 45 to the rear of the compartment. In the position of drive plate 50 when, momentarily, two rollers 51 engage two adjacent cut outs peg 76 is carried as far forward as possible. The turntable has then rotated by half the angle between cut-outs. Thus the drive assembly adopts one of two radial positions depending on the state of engagement with the cut-outs. The oscillatory motion of peg 76 is coupled via a link arm 77 to a pin 78 on the underside of carriage 66. Link 77 is slotted at pin 78 and preloaded by a spring (not shown) against the pin 78 to eliminate backlash at this point and to allow the carriage to be deflected across the ranks of locations by hand.

A ferrule 79 is fixed around the outside of sample tube 28 and is retained in a slot in the end of a member 80 attached to a slider 81. Slider 81 runs vertically on a rod 82 fixed to the carriage 66 and is restrained from rotation about rod 82 by a leaf 83 running in a vertical slot (not shown) in carriage 66. A stepping motor 84 with a threaded output shaft 85 is attached to carriage 66 and drives the slider 81 via a cord 86 which passes over a pulley 88 and is attached to a spring 87. Cord 86 makes a few turns around shaft 85 in the threads, spring 87 maintaining tension in the cord to ensure that the tension multiplying or "capstan" effect is obtained. At the start of sampling operations, more than sufficient stepping pulses are applied to motor 84 by external control means to drive slider 81 to the bottom of its travel in the position shown. The "capstan" effect on shaft 85 ensures that the cord does not slip on the shaft and the motor 84 stalls. The stepping pulses are removed and a counter in the external control means is zeroed, providing a reference count corresponding to the sample tube 28 being fully inserted in a container 21. The tube is withdrawn by applying a fixed number of stepping pulses to motor 84 in the reverse direction sufficient to retract the tube but not enough to drive slider 81 against its upper limit when the "capstan" effect would have been lost, cord 86 slipping on shaft 85 with loss of the tube reference position.

The turntable need not be fully loaded with sample containers and, accordingly, means are provided in the sampling mechanism for detecting when a container is absent as a location passes under the sample tube 28 and for providing a signal to inhibit sampling at this location. The container sensor arm 23 is pivoted about the bottom end of rod 82 via a universal coupling 88′ which allows sensor 23 to be deflected vertically as well as horizontally. Sensor 23 is resiliently restrained in a null position adjacent to the sample tube 28 by a spring 89 rigidly connected at one end to carriage 16 and at the other end to sensor 23. If a container is absent when the carriage 66 is moved over one or the other rank of locations, the sensor arm is not deflected from its null position. An opaque vane 90 attached to sensor 23 cooperates with an opto-electronic detector 91 of the same kind used in the door state detector and the cut-out detector described above. A binary output signal is available from detector 91, indicating by either of its two values whether a container is present or not, which can be fed to the external control means.

Figure 6:
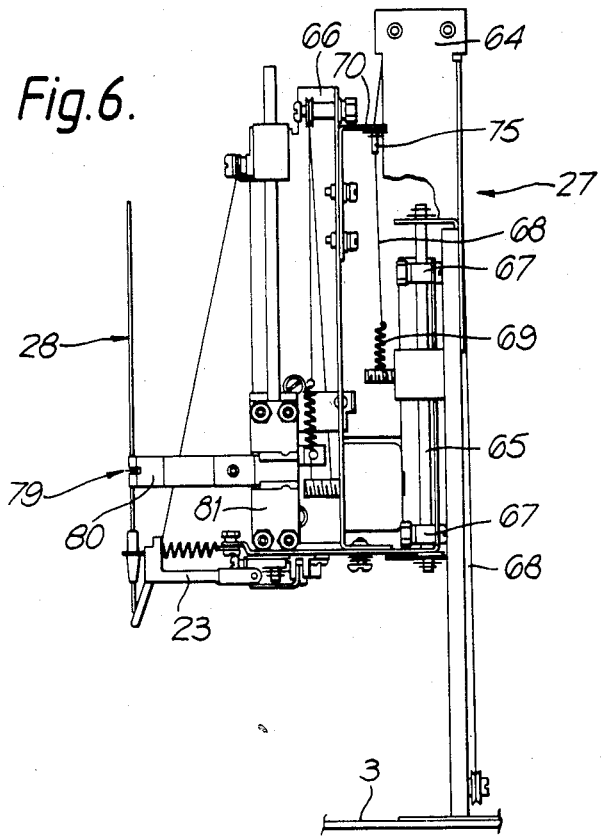
FIG. 6 shows a front view of the sampling mechanism.
Figure 7:
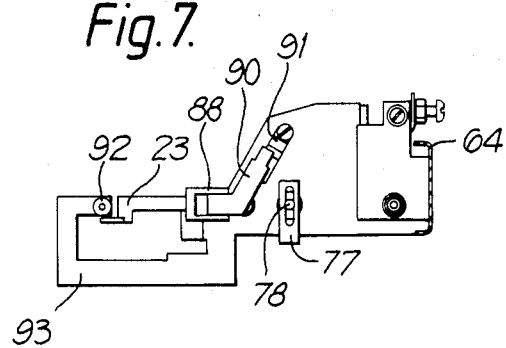
FIGS. 7 and 8 show top and bottom plan views of the sampling mechanism.
Figure 8:
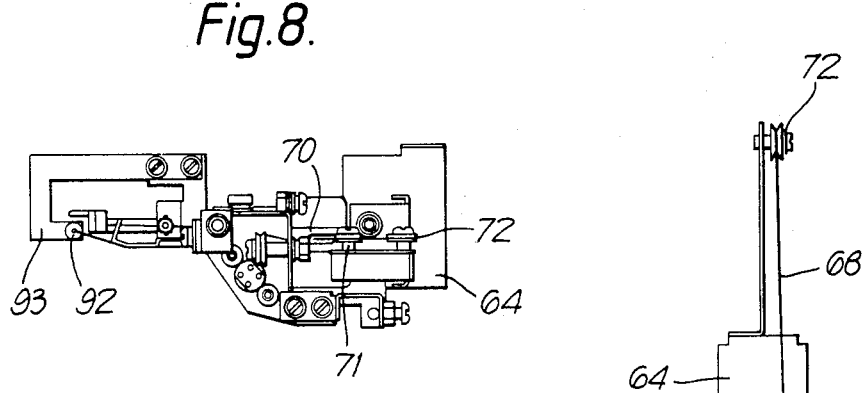
Figure 9:
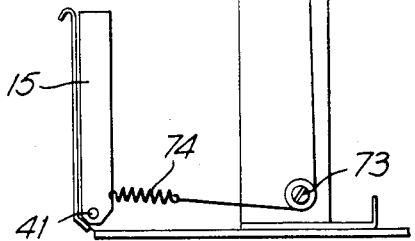
FIG. 9 shows a side view of part of the sampling mechanism.
Figure 10:
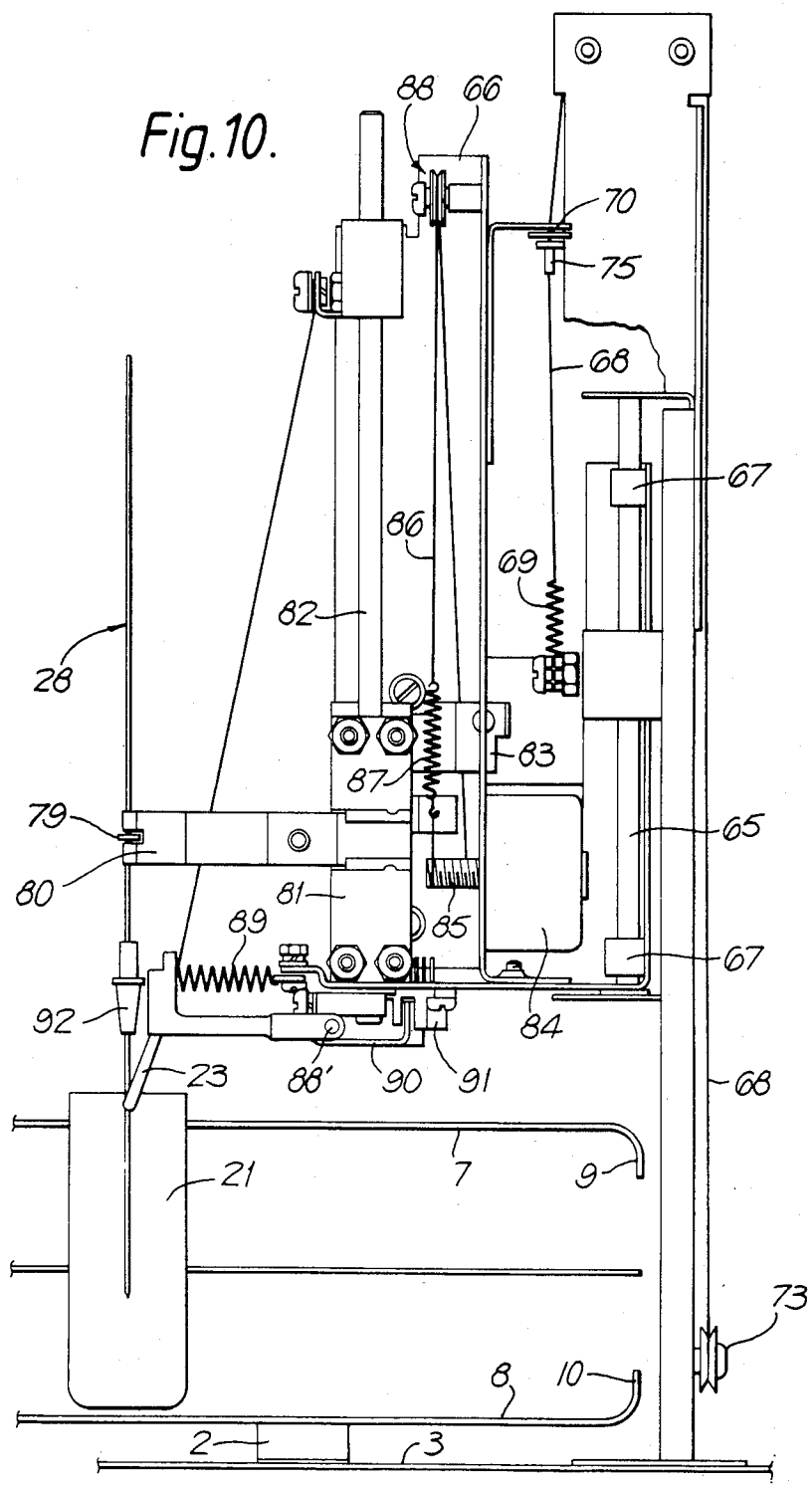
FIG. 10 shows an enlarged front view of the sampling mechanism.

The sample tube 28 is restrained in position at its lower end immediately above the container by a guide tube 92 held in position by a cranked arm 93 shown in FIGS. 7 and 8 but not in FIGS. 6 and 10 for clarity.

Driving assembly motor 47 and sampling stepper motor 84 are preferably placed under the control of a programmed calculator such as a microprocessor which may be the microprocessor as described in U.K. Patent Application Nos. 8133968 (PHB 32832) 8201371 (PHB 32848) and 8201372 (PHB 32849) which describe aspects of the atomic absorption spectrophotometer manufactured and sold by Pye Unicam Limited under the type number PU9000. Such a microprocessor is then connected to receive inputs from the door state sensor 43, the cut-out detector 22, and the container sensor 23. In accordance with a stored programme the microprocessor can then initiate turntable rotation and sample tube insertion automatically.

We claim:

1. An automatic sampling arrangement for supplying liquid samples to an analytical instrument comprising a compartment within which a sample carrier in the form of a turntable may be located, the turntable having a plurality of locations for sample containers arranged on a circle coaxial with the axis of rotation of the turntable, and a sampling mechanism for aspirating a sample from a sample container when the turntable is indexed to bring one of the sample locations in registration therewith, characterized in that the arrangement is constructed so that the turntable is inserted, in operation, into the compartment in a direction perpendicular to its axis of rotation, that the turntable is located by three bearing surfaces which engage the circumference of the turntable, that a driving assembly is provided which engages said circumference to rotate the turntable, and that one of the bearing surfaces is movable from a first position in which it engages said circumference to a second position to allow insertion or withdrawal of the turntable.

2. An automatic sampling arrangement as claimed in claim 1, characterized in that one of the three bearing surfaces comprises said driving assembly.

3. An automatic sampling arrangement as claimed in claim 1 or claim 2, characterized in that one of said bearing surfaces is mounted so as to resiliently urge the turntable into engagement with the other two bearing surfaces.

4. An automatic sampling arrangement as claimed in claim 1 or claim 2, characterized in that said bearing surfaces are rollers mounted for rotation about axes parallel to the turntable axis, and in that the rollers engage a cylindrical portion of the circumference.

5. An automatic sampling arrangement as claimed in claim 1 or claim 2 characterized in that cut-outs are provided at intervals around the circumference and in that the driving assembly comprises means for engaging the cut-outs to impart tangential motion to the circumference.

6. An automatic sampling arrangement as claimed in claim 5, characterized in that the cut-outs are spaced at intervals around the circumference corresponding to the spacing of sample locations around the turntable, and in that a cut-out detector is provided in said compartment to generate a control signal for the driving assembly when a desired sample location is in registration with the sampling mechanism.

7. An automatic sampling arrangement as claimed in claim 1 or claim 2 characterized in that the compartment comprises an aperture, closable by a door, through which the turntable is inserted, and in that the door is coupled to the movable bearing surface so that with the door open the movable bearing surface is in its second position and with the door closed the movable bearing surface is in its first position.

8. An automatic sampling arrangement as claimed in claim 1 or claim 2, characterized in that the turntable rests on a floor of the compartment.

9. An automatic sampling arrangement as claimed in claim 8, characterized in that there are low friction pads between the turntable base and the floor.

10. An automatic sampling arrangement as claimed in claim 9, characterized in that the pads are attached to the floor.

11. An automatic sampling arrangement as claimed in claim 10, characterized in that there are three pads evenly spaced around a circle centered on the turntable axis.

* * * * *